(12) United States Patent
Olubummo et al.

(10) Patent No.: US 11,383,433 B2
(45) Date of Patent: *Jul. 12, 2022

(54) FUSING AGENT(S)

(71) Applicant: Hewlett-Packard Development Company, L.P., Spring, TX (US)

(72) Inventors: Adekunle Olubummo, Palo Alto, CA (US); Aja Hartman, Palo Alto, CA (US); Lihua Zhao, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 408 days.

This patent is subject to a terminal disclaimer.

(21) Appl. No.: 16/475,534

(22) PCT Filed: Apr. 17, 2017

(86) PCT No.: PCT/US2017/027881
§ 371 (c)(1),
(2) Date: Jul. 2, 2019

(87) PCT Pub. No.: WO2018/194542
PCT Pub. Date: Oct. 25, 2018

(65) Prior Publication Data
US 2019/0382429 A1      Dec. 19, 2019

(51) Int. Cl.
*C07F 15/04*      (2006.01)
*B29C 64/165*      (2017.01)
(Continued)

(52) U.S. Cl.
CPC ............ *B29C 64/165* (2017.08); *B33Y 10/00* (2014.12); *B33Y 70/00* (2014.12); *C09D 11/38* (2013.01)

(58) Field of Classification Search
CPC .... C07F 15/045; C07F 321/18; B29C 64/165; B29C 64/214; B29C 64/218; B29C 64/393; B33Y 10/00; B33Y 70/00
See application file for complete search history.

(56) References Cited

U.S. PATENT DOCUMENTS 3,875,199 A      4/1975 Bloom
5,024,923 A  *  6/1991 Suzuki .................... C09D 5/32
                                                                    252/587

(Continued)

FOREIGN PATENT DOCUMENTS

CN        101233208 A      7/2008
CN        101466719 A      6/2009
(Continued)

OTHER PUBLICATIONS

Aragoni, M.C. et al., NIR Dyes Based on [M(R,R'timdt)2] Metal-Dithiolenes: Additivity of M, R, and R' Contributions to Tune the NIR Absorption (M=Ni, Pd, Pt: R,R'timdt= Monoreduced Form of Disubstituted Imidazolidine-2,4,5-trithione). May 13, 2003, < http://onlinelibrary.wiley.com/doi/10.1002/ellc.200200602/full >.

(Continued)

*Primary Examiner* — Bijan Ahvazi
(74) *Attorney, Agent, or Firm* — HPI Patent Department

(57) ABSTRACT

Fusing agent(s) are described herein. In an example, a fusing agent can comprise a metal bis(dithiolene) complex, at least one electron donor compound, a polar aprotic solvent, and water. In some examples, the at least one electron donor compound can comprise at least one hindered amine light stabilizer compound. In some examples, the polar aprotic solvent can be selected from the group consisting of 1-methyl-2-pyrrolidone, 2-pyrrolidone, 1-(2-hydroxyethyl)-2-pyrrolidone, dimethylformamide (DMF), dimethyl sulfoxide (DMSO), and a combination thereof.

10 Claims, 2 Drawing Sheets

(51) Int. Cl.
*B33Y 10/00* (2015.01)
*B33Y 70/00* (2020.01)
*C09D 11/38* (2014.01)

(56) References Cited

U.S. PATENT DOCUMENTS

| | | | |
|---|---|---|---|
| 7,026,017 B2 | 4/2006 | Wolf et al. | |
| 7,204,941 B2 | 4/2007 | Hall et al. | |
| 7,282,164 B2 | 10/2007 | Hall et al. | |
| 8,853,314 B2 | 10/2014 | Mamak et al. | |
| 9,144,940 B2 | 9/2015 | Martin et al. | |
| 9,260,614 B2 * | 2/2016 | Reichelt | C07D 233/84 |
| 9,482,974 B2 | 11/2016 | Martin | |
| 10,780,633 B2 * | 9/2020 | Olubummo | B29C 64/214 |
| 10,781,228 B2 * | 9/2020 | Olubummo | C07F 15/045 |
| 2004/0196344 A1 | 10/2004 | Hall et al. | |
| 2009/0121031 A1 | 5/2009 | Hall et al. | |
| 2012/0313058 A1 | 12/2012 | Masuhara et al. | |
| 2016/0198576 A1 * | 7/2016 | Lewis | H01L 24/75 361/761 |
| 2016/0333181 A1 * | 11/2016 | Sybert | B32B 27/08 |
| 2017/0022349 A1 | 1/2017 | Mii et al. | |
| 2019/0092799 A1 | 3/2019 | Olubummo et al. | |

FOREIGN PATENT DOCUMENTS

| | | | | |
|---|---|---|---|---|
| CN | 101610893 A | 12/2009 | | |
| DE | 4202037 A1 | 7/1993 | | |
| EP | 0408908 A1 | 1/1991 | | |
| EP | 0410443 B | 1/1995 | | |
| EP | 2942378 B1 | 8/2016 | | |
| EP | 3067216 A1 | 9/2016 | | |
| WO | WO-2009059900 A2 | 5/2009 | | |
| WO | WO-2010046285 A2 | 4/2010 | | |
| WO | WO-2012069518 | 5/2012 | | |
| WO | WO-2016068899 A1 * | 5/2016 | | B29C 67/247 |
| WO | WO-2017014785 A1 | 1/2017 | | |
| WO | WO-2017023283 A1 | 2/2017 | | |

OTHER PUBLICATIONS

Fy, J. et al., Strong two-phonon absorption at telecommunications wavelengths in nickel bis(dithiolene) complexes, Opics Letters, 2007, Vo. 32, No. 6, pp. 671-673, especially p. 671, fig. 1,3.

Mebrouk, K et al., Water-soluble nickel-bis (dithiolene) complexes as photothermal agents. Chem. Commun. 2014, DOI: 10-1039/c4cc08231a, pp. 1-3 especially fig. 1,2.

* cited by examiner

FUSING AGENT(S)

BACKGROUND

Three-dimensional (3D) printing can be an additive printing process used to make three-dimensional object(s) or part(s) from a digital model. 3D printing is often used in rapid product prototyping, mold generation, and mold master generation. Some 3D printing techniques are considered additive processes because they involve the application of successive layers of material. This is unlike machining processes, which tend to rely upon the removal of material to create the final part.

Materials used in 3D printing tend to need curing or fusing, which for some materials may be accomplished using heat-assisted extrusion or sintering, and for other materials may be accomplished using digital light projection technology.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1A:
FIGS. 1A and 1B show pictures of fusing agent compositions exhibiting no phase separation (FIG. 1A) and exhibiting phase separation (FIG. 1B).

Examples of the three-dimensional (3D) printing method disclosed herein utilize Multi Jet Fusion Printing (MJFP). During MJFP, a layer of a build material (also referred to as build material particles) is exposed to radiation, but a selected region (in some instances less than the entire layer) of the build material is fused and hardened to become a layer of a 3D part(s) or object(s).

A fusing agent (e.g., carbon black) can be selectively deposited in contact with the selected region of the build material. The fusing agent(s) is capable of penetrating into the layer of the build material and spreading onto the exterior surface of the build material. This fusing agent is capable of absorbing radiation and converting the absorbed radiation to thermal energy, which in turn melts or sinters the build material that is in contact with the fusing agent. This causes the build material to fuse, bind, cure, etc. to form the layer of the 3D part.

As used herein, the terms "3D printed part," "3D part," "part," "3D printed object," "3D object," or "object" may be a completed 3D printed part or a layer of a 3D printed part.

As used herein, "(s)" at the end of some terms indicates that those terms/phrases may be singular in some examples or plural in some examples. It is to be understood that the terms without "(s)" may be also be used singularly or plurally in many examples.

Some fusing agents used in MJFP tend to have significant absorption (e.g., 80%) in the 700 nm-1400 nm light absorbing range. This absorption generates heat suitable for fusing during 3D printing, which leads to 3D parts having mechanical integrity and relatively uniform mechanical properties (e.g., strength, elongation at break, etc.). This absorption, however, results in strongly colored, e.g., black, 3D parts. In some instances, it may not be necessary to generate strongly colored parts. Rather, it may be appropriate to generate a part that is clear, white, off-white, or some color other than black.

To meet the MJFP process(es) for a fusing agent and printing colorless or white parts, a near-infrared dye should be physically and chemically stable, compatible with ink vehicles and co-solvents to give a good jetting performance, and colorless after printing. Nickel bis(dithiolene) in its neutral state is a good near-infrared material to use in MJFP but it is not water soluble and has a green color.

Nickel bis(dithiolene) can be reduced to the monoanion state to become water soluble and with further reduction to a dianion, nickel bis(dithiolene) becomes colorless. Nickel bis(dithiolene) can be reduced with secondary or tertiary amines. However, the reduction process is slow even at higher temperatures of about 80° C. to about 100° C. because these complexes are partially soluble in such amines.

In some examples, dodecanethiol can be used as a surfactant to bring the metal bis(dithiolene) complex into the amine (e.g., hydroxyethyl-2-pyrrolidone) phase, which can result in reducing the complex to its monoanion state within seconds. Dodecanethiol is, however, needed in an amount of at least about 3 wt % to 5 wt % based on the total weight of the fusing agent to enhance the reduction. This amount of dodecanethiol can cause phase separation in the fusing agent composition.

In some examples, the fusing agent containing dodecanethiol can also have a rotten egg smell, which is not pleasant to work with and the 3D printed part may also have a rotten egg smell due to the residual dodecanethiol in the part. This would not be widely commercially appropriate.

In some examples, using hydroxyethyl-2-pyrrolidone can cause thermal inkjet performance issues due to its high viscosity.

To address at least some of the above-described issues, fusing agents described herein below exhibit a reduced viscosity compared with other known fusing agents and can therefore result in better thermal inkjet performance. Fusing agents described in the examples below further show that when thiol surfactants (e.g., dodecanethiol) are replaced with an electron donor compound (e.g., hindered amine light stabilizers), phase separation is reduced and issues with rotten egg smell emanation are eliminated.

The electron donor compounds described herein below (e.g., hindered amine light stabilizers) can also stabilize the build material against degradation by photo-oxidation after a 3D printed part or object is obtained.

Fusing Agent(s) Including Metal Bis(Dithiolene) Complex(es)

Examples of a fusing agent can include a fusing agent comprising a metal bis(dithiolene) complex, at least one electron donor compound, a polar aprotic solvent, and water.

In some examples, a fusing agent can comprise:
a metal bis(dithiolene) complex;
at least one electron donor compound;
a polar aprotic solvent; and
water.

Examples of the fusing agent disclosed herein can contain a metal bis(dithiolene) complex, which can absorb light having wavelengths ranging from about 600 nm to about 1600 nm. The metal bis(dithiolene) complex, and the fusing agent including the complex, is capable of absorbing at least about 80% of radiation having wavelengths ranging from about 600 nm to about 1600 nm.

The absorption maximum of the metal bis(dithiolene) complex may undergo a bathochromic shift (e.g., further into the near-infrared region toward the medium infrared region) or a hypsochromic shift (e.g., in the near-infrared region toward the visible region) depending upon the chemistry of the complex and/or fusing agent. As examples, the shift may depend upon a polar aprotic solvent present in the fusing agent and/or upon the nature of the functional group(s) attached to the complex. Like the visible region absorbing fusing agents, the absorption of the fusing agents including the metal bis(dithiolene) complex generates heat suitable for fusing polymeric or polymeric composite build material in contact therewith during 3D printing, which leads to 3D parts having mechanical integrity and relatively uniform mechanical properties (e.g., strength, elongation at break, etc.).

The metal bis(dithiolene) complex allows the fusing agent to absorb radiation at wavelengths ranging from 600 nm to 1600 nm, which enables the fusing agent to convert enough radiation to thermal energy so that the polymeric or polymeric composite build material particles in contact with the fusing agent fuse.

Examples of the metal bis(dithiolene) complex may have a general formula I:

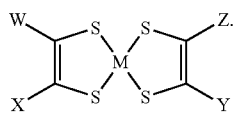

(I)

Examples of M include nickel, zinc, platinum, palladium, and molybdenum. Examples of each of W, X, Y, and Z include a hydrogen (H), a phenyl group (Ph), a phenyl group bonded to an R group (i.e., PhR), wherein R is $C_nH_{2n+1}$, or $OC_nH_{2n+1}$, or $N(CH_3)_2$, and a sulfur bonded to an R group (i.e., SR), wherein R is $C_nH_{2n+1}$, or $OC_nH_{2n+1}$, or $N(CH_3)_2$. In these examples, n may be greater than or equal to 2 and less than or equal to 12 (i.e., $2 \leq n \leq 12$).

When the metal bis(dithiolene) complex has the general formula I shown above, the strong NIR absorption of the metal bis(dithiolene) complex may be the result of the electron delocalization about the dithiolene ring and the interaction of the delocalized electrons with the empty d-orbitals of the metal center.

The amount of the metal bis(dithiolene) complex in the fusing agent may range from about 1 wt % to about 10 wt % based on the total weight of the fusing agent. In an example, the amount of the metal bis(dithiolene) complex present in the fusing agent is from about 1 wt % to about 7 wt % based on the total weight of the fusing agent. In an example, the amount of the metal bis(dithiolene) complex present in the fusing agent is from about 2 wt % to about 5 wt % based on the total weight of the fusing agent. In an example, the amount of the metal bis(dithiolene) complex present in the fusing agent is less than about 5 wt % based on the total weight of the fusing agent. In an example, the amount of the metal bis(dithiolene) complex present in the fusing agent is less than about 4 wt % based on the total weight of the fusing agent. In an example, the amount of the metal bis(dithiolene) complex present in the fusing agent is less than about 3 wt % based on the total weight of the fusing agent.

These metal bis(dithiolene) complex loadings can generate a balance between the fusing agent having jetting reliability and electromagnetic radiation absorbance efficiency.

The polar aprotic solvent may be included in the fusing agent to at least partially dissolve and reduce the metal bis(dithiolene) complex and to shift the absorption of the metal bis(dithiolene) complex. In some instances, the shift can be further into the near-infrared (NIR) region (e.g., shifting from an absorption maximum of about 850 nm when the metal bis(dithiolene) complex is not reduced to an absorption maximum of about 940 nm when metal bis (dithiolene) complex is reduced (e.g., to its monoanionic form or to its dianionic form)). The electron donor compound can shift the absorption maximum of the metal bis(dithiolene) complex by reducing the metal bis(dithiolene) complex to its monoanionic form or to its dianionic form according to equation II shown below:

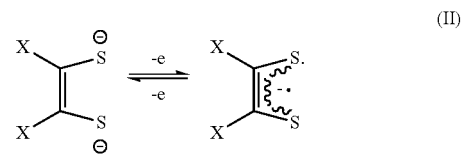

(II)

When the metal bis(dithiolene) complex is reduced to its monoanionic form or to its dianionic form, the color of the metal bis(dithiolene) complex can change. For example, the initial reduction of a nickel bis(dithiolene) complex to its monoanionic form may result in the color changing from green to reddish brown. For example, the further reduction of a nickel bis(dithiolene) complex to its dianionic form may result in the color changing to become substantially colorless. Other color changes may be observed with different metals in the complex. As noted above, the color changed complex can still absorb infrared radiation.

In some examples, the fusing agent can include:
the metal bis(dithiolene) complex is present in an amount ranging from about 1 wt % to about 10 wt % based on the total weight of the fusing agent;
the at least one electron donor compound is present in an amount ranging from about 1 wt % to about 10 wt % based on the total weight of the fusing agent; and
the polar aprotic solvent is present in an amount ranging from about 5 wt % to about 50 wt % based on the total weight of the fusing agent.

In some examples, a fusing agent can comprise:
a metal bis(dithiolene) complex having a general formula I:

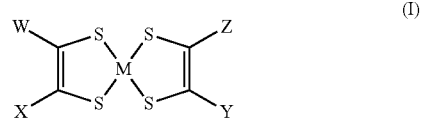

(I)

wherein:
M is a metal selected from the group consisting of nickel, zinc, platinum, palladium, and molybdenum; and
each of W, X, Y, and Z is selected from the group consisting of H, Ph, PhR, and SR, wherein Ph is a phenyl group and R is selected from the group consisting of $C_nH_{2n+1}$, $OC_nH_{2n+1}$, and $N(CH_3)_2$, wherein $2 \leq n \leq 12$;
a colorant;
at least one hindered amine light stabilizer compound;
a polar aprotic solvent comprising 2-pyrrolidone; and
water.

Polar Aprotic Solvent(s)

In some examples, the polar aprotic solvent can include 1-methyl-2-pyrrolidone (1M2P), 2-pyrrolidone, 1-(2-hydroxyethyl)-2-pyrrolidone, dimethylformamide (DMF), dimethyl sulfoxide (DMSO), and combinations thereof.

In some examples, the polar aprotic solvent is 2-pyrrolidone.

The polar aprotic solvent can be present in the fusing agent in an amount sufficient to reduce the metal bis(dithiolene) complex to its monoanionic form or to its dianionic form. In an example, the amount of the polar aprotic solvent in the fusing agent may range from about 5 wt % to about 70 wt % based on the total weight of the fusing agent. In an example, the amount of the polar aprotic solvent in the fusing agent may range from about 15 wt % to about 60 wt % based on the total weight of the fusing agent. In an example, the amount of the polar aprotic solvent in the fusing agent may range from about 25 wt % to about 50 wt % based on the total weight of the fusing agent. In an example, the amount of the polar aprotic solvent in the fusing agent may range from about 35 wt % to about 45 wt % based on the total weight of the fusing agent. In another example, the amount of the polar aprotic solvent present in the fusing agent is about 40 wt % based on the total weight of the fusing agent. In still another example, the amount of the polar aprotic solvent present in the fusing agent is about 50 wt % based on the total weight of the fusing agent.

Electron Donor Compound(s)

The fusing agent(s) described herein can include at least one electron donor compound. In some examples, the electron donor compound can comprise at least one hindered amine light stabilizer (HALS) compound.

The HALS term is a general term for compounds that can have a 2,2,6,6-tetramethylpiperidine skeleton and are broadly categorized according to molecular weight into low-molecular weight HALSs, medium-molecular weight HALSs, high-molecular weight HALSs and reactive HALSs.

Examples of HALS compounds can include TINUVIN® 111 FDL, TINUVIN® 123, TINUVIN® 144, TINUVIN® 292, TINUVIN® 765, TINUVIN® 770 (i.e., bis(2,2,6,6,-tetramethyl-4-piperidyl)sebacate), and mixtures thereof, all from BASF Corp.

Examples of HALS compounds can also include N,N'-bis(3-aminopropyl)ethylenediamine-2,4-bis[N-butyl-N-(1,2,2,6,6-penta-methyl-4-piperidyl)amino]-6-chloro-1,3,5-triazine condensate (CHIMASSORB® 119), CHIMASSORB® 2020, dimethyl succinate-1-(2-hydroxyethyl)-4-hydroxy-2,2,6,6-tetramethyl piperidine polycondensate (CHIMASSORB® 622LD), poly[{6-(1,1,3,3-tetramethyl-butyl)amino-1,3,5-triazine-2,4-diyl}{(2,2,6,-6-tetramethyl-4-piperidyl)imino}hexamethylene{(2,2,6,6-tetramethyllauryl-4-piperidyl)imino}] (CHIMASSORB® 944FD), and mixtures thereof, all from BASF Corp.

Examples of HALS compounds can also include Sanduvor® 3050 Liq., Sanduvor® 3052 Liq., Sanduvor® 3058 Liq., Sanduvor® 3051 Powder, Sanduvor® 3070 Powder, VP Sanduvor® PR-31, HOSTAVIN® N20, HOSTAVIN® N24, HOSTAVIN® N30, HOSTAVIN® N321, HOSTAVIN® PR-31, HOSTAVIN® 845, NYLOSTAB® S-EED®, and mixtures thereof, all from Clariant (Japan) K.K.

In some examples, the electron donor compound is TINUVIN® 770 (i.e., bis(2,2,6,6,-tetramethyl-4-piperidyl)sebacate).

In some examples, the electron donor compound(s) described herein can facilitate the reduction of the metal bis(dithiolene) complex in combination with a polar aprotic solvent described herein. Without wishing to be bound by theory, the electron donor compound can render the metal bis(dithiolene) complex readily reducible and thus more soluble in the polar aprotic solvent. Without the electron donor compound, the reduction of the metal bis(dithiolene) complex to its monoanionic form or to its dianionic form may involve the mixture of the neutral, non-reduced metal bis(dithiolene) complex and the polar aprotic solvent to be heated to an elevated temperature (e.g., a temperature ranging from about 50° C. to about 200° C.) for an extended time period (e.g., a time period ranging from about 5 hours to about 48 hours). However, when the electron donor compound is included in the mixture of the metal bis(dithiolene) complex and the polar aprotic solvent, the reduction of the metal bis(dithiolene) complex to its monoanionic form or to its dianionic form may be achieved at room temperature (e.g., from about 18° C. to about 25° C.) and within a few seconds (e.g., less than 10 seconds).

The electron donor compound(s) may also improve the jettability of the fusing agent by stabilizing the metal bis(dithiolene) complex. Without the electron donor compound(s), the metal bis(dithiolene) complex may precipitate out of solution when water or a liquid vehicle is added. When the electron donor compound(s) is included in the mixture of the metal bis(dithiolene) complex and the polar aprotic solvent, the reduced metal bis(dithiolene) complex can be easily formulated into (i.e., dissolved or dispersed rather than precipitated out of) a liquid vehicle.

The electron donor compound(s) can be present in the fusing agent in an amount sufficient to reduce and/or stabilize the metal bis(dithiolene) complex. In an example, the amount of the electron donor compound(s) in the fusing agent may range from about 1 wt % to about 10 wt % based on the total weight of the fusing agent. In an example, the amount of the electron donor compound(s) in the fusing agent may range from about 2 wt % to about 7 wt % based on the total weight of the fusing agent. In an example, the amount of the electron donor compound(s) in the fusing agent may range from about 3 wt % to about 5 wt % based on the total weight of the fusing agent. In an example, the amount of the electron donor compound(s) in the fusing agent may range from about 3 wt % to about 4 wt % based on the total weight of the fusing agent.

Fluid Vehicle & Additive(s)

The fusing agent disclosed herein can include a liquid vehicle. Liquid vehicle(s), as described herein, can include the aprotic solvent(s) described hereinabove and solvent(s) other than the aprotic solvent(s) described hereinabove. The liquid vehicle(s), as described herein, can generally include solvent(s) in which the metal bis(dithiolene) complex is placed to form the fusing agent.

Examples of fluid vehicles can include water, alone or in combination with a mixture of a variety of additional components. Examples of these additional components may include water soluble co-solvent(s), wetting agent(s), surface tension reduction agent(s), emulsifier(s), scale inhibitor(s), anti-deceleration agent(s), chelating agent(s), and/or antimicrobial agent(s).

In some examples, the fluid vehicle can be present in the fusing agent in an amount of from about 1 wt % to about 80 wt % based on the total weight of the fusing agent. In some examples, the fluid vehicle can be present in the fusing agent in an amount of from about 5 wt % to about 70 wt % based on the total weight of the fusing agent. In some examples, the fluid vehicle can be present in the fusing agent in an amount of from about 10 wt % to about 60 wt % based on the total weight of the fusing agent. In some examples, the fluid vehicle can be present in the fusing agent in an amount of from about 20 wt % to about 50 wt % based on the total weight of the fusing agent. In some examples, the fluid vehicle can be present in the fusing agent in an amount of from about 50 wt % to about 95 wt % based on the total weight of the fusing agent. In some examples, the fluid vehicle can be present in the fusing agent in an amount of from about 60 wt % to about 85 wt % based on the total weight of the fusing agent.

The co-solvent can be present in the fluid vehicle in an amount ranging from about 0.1 wt % to about 20 wt % based on the total weight of the fluid vehicle.

Some examples of co-solvents can include 2-pyrrolidinone, hydroxyethyl-2-pyrrolidone, diethylene glycol, 2-methyl-1,3-propanediol, tetraethylene glycol, tripropylene glycol methyl ether, dipropylene glycol methyl ether, tripropylene glycol butyl ether, dipropylene glycol butyl ether, triethylene glycol butyl ether, 1,2-hexanediol, 2-hydroxyethyl pyrrolidinone, 2-hydroxyethyl-2-pyrrolidinone, 1,6-hexanediol, and combinations thereof.

One example fluid vehicle includes water, the polar aprotic solvent, and the electron donor compound(s). Another example fluid vehicle consists of water, the polar aprotic solvent, and the electron donor compound(s) (without any other components).

The water in the fluid vehicle may prevent (further) reduction of the metal bis(dithiolene) complex until the water is driven off as a result of the build material platform temperature and/or the temperature achieved during radiation exposure. After the water is driven off, the metal bis(dithiolene) complex is capable of being further reduced and becoming colorless/discolored, which enables the 3D part to exhibit a color of the build material (e.g., white or off-white) or to exhibit a color of a colorant present in the fusing agent.

The aqueous nature of the fusing agent can enable the fusing agent to penetrate, at least partially, into the layer of the polymeric or polymeric composite build material particles. The build material particles may be hydrophobic, and the presence of the wetting agent(s) in the fusing agent may assist in obtaining a particular wetting behavior.

The balance of the fusing agent is water. As such, the amount of water may vary depending upon the amounts of the metal bis(dithiolene) complex, the electron donor compound, the polar aprotic solvent, any colorant(s), any dispersant(s), any co-solvent(s), and in some instances antikogation agent(s), the additive dispersant(s), the acrylic latex binder(s), and/or the biocide(s) that can be included.

In some examples, water can be present in the fusing agent(s) in amounts greater than about 30 wt % based on the total weight of the fusing agent(s). In some examples, the water can be present in the fusing agent(s) in amounts from about 40 wt % to about 90 wt % based on the total weight of the fusing agent(s). In other examples, the fusing agent(s) can include from about 45 wt % to about 80 wt % water. In further examples, the fusing agent(s) can include from about 50 wt % to about 70 wt % water.

Examples of suitable wetting agents can include non-ionic surfactants. Some specific examples include a self-emulsifiable, non-ionic wetting agent based on acetylenic diol chemistry (e.g., SURFYNOL® SEF from Air Products and Chemicals, Inc.), a non-ionic fluorosurfactant (e.g., CAPSTONE® fluorosurfactants from DuPont, previously known as ZONYL FSO), and combinations thereof. In other examples, the wetting agent is an ethoxylated low-foam wetting agent (e.g., SURFYNOL® 440 or SURFYNOL® CT-111 from Air Products and Chemical Inc.) or an ethoxylated wetting agent and molecular defoamer (e.g., SURFYNOL® 420 from Air Products and Chemical Inc.). Still other suitable wetting agents include non-ionic wetting agents and molecular defoamers (e.g., SURFYNOL® 104E from Air Products and Chemical Inc.) or water-soluble, non-ionic surfactants (e.g., TERGITOL™ TMN-6, TERGITOL™ 15S7, and TERGITOL™ 15S9 from The Dow Chemical Company). In some examples, an anionic surfactant may be used in combination with the non-ionic surfactant. In some examples, it may be appropriate to utilize a wetting agent having a hydrophilic-lipophilic balance (HLB) less than 10.

The wetting agent(s) may be present in the fusing agent in an amount ranging from about 0.1 wt % to about 4 wt % of the total weight of the fusing agent. In an example, the amount of the wetting agent(s) present in the fusing agent is about 0.1 wt % (based on the total weight of the fusing agent). In another example, the amount of the wetting agent(s) present in the fusing agent is about 0.04 wt % (based on the total weight of the fusing agent).

The fluid vehicle may also include surface tension reduction agent(s). Any of the previously mentioned wetting agents/surfactants may be used to reduce the surface tension. As an example, the surface tension reduction agent may be the self-emulsifiable, non-ionic wetting agent based on acetylenic diol chemistry (e.g., SURFYNOL® SEF from Air Products and Chemicals, Inc.).

The surface tension reduction agent(s) may be present in the fusing agent in an amount ranging from about 0.1 wt % to about 4 wt % of the total weight of the fusing agent. In an example, the amount of the surface tension reduction agent(s) present in the fusing agent is about 1.5 wt % (based on the total weight of the fusing agent). In another example, the amount of the surface tension reduction agent(s) present in the fusing agent is about 0.6 wt % (based on the total weight of the fusing agent).

When a surfactant is both a wetting agent and a surface tension reduction agent, any of the ranges presented herein for the wetting agent and the surface tension reduction agent may be used for the surfactant.

The fluid vehicle may also include water soluble organic solvent(s). In some examples, the water soluble organic solvent(s) may be the same type of solvent as the polar aprotic solvent. In these examples, the water soluble organic solvent(s) may be 1-methyl-2-pyrrolidone (1M2P), 2-pyrrolidone, 1-(2-hydroxyethyl)-2-pyrrolidone, dimethylformamide (DMF), dimethyl sulfoxide (DMSO), or a combination thereof. In other examples, the water soluble organic solvent(s) may be different than the polar aprotic solvent. For example, two different polar aprotic solvents may be selected. For another example, the water soluble organic solvent(s) may be 1,5-pentanediol, triethylene glycol, tetraethylene glycol, 2-methyl-1,3-propanediol, 1,6-hexanediol, tripropylene glycol methyl ether, or a combination thereof.

The water soluble organic solvent(s) may be present in the fusing agent in an amount ranging from about 2 wt % to about 80 wt % of the total weight of the fusing agent. In an example, the amount of the water soluble organic solvent(s)

present in the fusing agent is about 40 wt % (based on the total weight of the fusing agent). In another example, the amount of the water soluble organic solvent(s) present in the fusing agent is about 16 wt % (based on the total weight of the fusing agent).

The fluid vehicle may also include emulsifier(s). Examples of suitable emulsifiers include oleth-3-phosphate (commercially available as CRODAFOS™ O3A or CRODAFOS™ N-3 acid) or dextran 500 k. Other suitable examples of the emulsifiers include CRODAFOS™ HCE (phosphate-ester from Croda Int.), CRODAFOS® N10 (oleth-10-phosphate from Croda Int.), etc.

The emulsifier(s) may be present in the fusing agent in an amount ranging from about 0.1 wt % to about 2 wt % of the total weight of the fusing agent. In an example, the amount of the emulsifier(s) present in the fusing agent is about 1 wt % (based on the total weight of the fusing agent). In another example, the amount of the emulsifier(s) present in the fusing agent is about 0.4 wt % (based on the total weight of the fusing agent).

The fusing agent may include scale inhibitor(s) or anti-deceleration agent(s). One suitable scale inhibitor/anti-deceleration agent is an alkyldiphenyloxide disulfonate (e.g., DOWFAX™ 8390 and DOWFAX™ 2A1 from The Dow Chemical Company).

The scale inhibitor(s)/anti-deceleration agent(s) may be present in the fusing agent in an amount ranging from about 0.05 wt % to about 5 wt % of the total weight of the fusing agent. In an example, the scale inhibitor(s)/anti-deceleration agent(s) is/are present in the fusing agent in an amount of about 0.25 wt % (based on the total weight of the fusing agent). In another example, the scale inhibitor(s)/anti-deceleration agent(s) is/are present in the fusing agent in an amount of about 0.1 wt % (based on the total weight of the fusing agent).

The fusing agent may also include chelating agent(s). The chelating agent may be included to eliminate the deleterious effects of heavy metal impurities. Examples of suitable chelating agents include disodium ethylenediaminetetraacetic acid (EDTA-Na), ethylene diamine tetra acetic acid (EDTA), and methylglycinediacetic acid (e.g., TRILON® M from BASF Corp.).

Whether a single chelating agent is used or a combination of chelating agents is used, the total amount of chelating agent(s) in the fusing agent may range from 0 wt % to about 2 wt % based on the total weight of the fusing agent. In an example, the chelating agent is present in the fusing agent in an amount of about 0.08 wt % (based on the total weight of the fusing agent). In another example, the chelating agent is present in the fusing agent in an amount of about 0.032 wt % (based on the total weight of the fusing agent).

The fluid vehicle may also include antimicrobial agent(s). Suitable antimicrobial agents include biocides and fungicides. Example antimicrobial agents may include the NUOSEPT® (Ashland Inc.), UCARCIDE™ or KORDEK™ (Dow Chemical Co.), and PROXEL® (Arch Chemicals) series, ACTICIDE® M20 (Thor), and combinations thereof.

In an example, the fusing agent may include a total amount of antimicrobial agents that ranges from about 0.1 wt % to about 0.35 wt %. In an example, the antimicrobial agent is a biocide and is present in the fusing agent in an amount of about 0.32 wt % (based on the total weight of the fusing agent). In another example, the antimicrobial agent is a biocide and is present in the fusing agent in an amount of about 0.128 wt % (based on the total weight of the fusing agent).

The balance of the fusing agent is water. As an example, deionized water may be used.

In an example, the fusing agent includes from about 1 wt % to about 3 wt % of the metal bis(dithiolene) complex, from about 1 wt % to about 5 wt % of the electron donor compound(s), from about 5 wt % to about 50 wt % of the polar aprotic solvent, and a balance of water (based on the total weight of the fusing agent).

Colorant(s)

In some examples, the fusing agent may further include a colorant. The colorant can be present in the fusing agent in addition to the metal bis(dithiolene) complex. While the metal bis(dithiolene) complex functions as an electromagnetic radiation absorber and becomes colorless after fusing the build material, the additional colorant may impart color to the fusing agent and the resulting 3D part.

The colorant may be a pigment and/or dye having any suitable color. Examples of the colors include cyan, magenta, yellow, etc.

Examples of colorants include dyes, such as Acid Yellow 23 (AY 23), Acid Yellow 17 (AY 17), Acid Red 52 (AR 52), Acid Red 289 (AR 289), Reactive Red 180 (RR 180), Direct Blue 199 (DB 199), or pigments, such as Pigment Blue 15:3 (PB 15:3), Pigment Red 122 (PR 122), Pigment Yellow 155 (PY 155), and Pigment Yellow 74 (PY 74).

Any standard color pigments may be used, such as phthalocyanines for blue, quinacridone for magenta or red, pigment yellow for yellow, white, black, or combinations thereof. Some commercially available examples of the white colorant are available from DuPont under the tradename TI-PURE®, an example of which includes TI-PURE® R-706.

In some examples, dyes can be used. Examples include acid dyes (e.g., Acid Red 52, Acid Red 289, Acid Yellow 23, Acid Yellow 17, or combinations thereof), reactive dyes (e.g., Reactive Red 180, Reactive Black 31, or combinations thereof), and phthalocyanine dyes (e.g., Direct Blue 199 and Pro-Jet Cyan dyes available from Fujifilm Industrial Colorants).

Some examples of the colorant(s) can include a set of cyan, magenta, and yellow inks, such as C1893A (cyan), C1984A (magenta), and C1985A (yellow); or C4801A (cyan), C4802A (magenta), and C4803A (yellow); all of which are available from Hewlett-Packard Company.

In some other examples, the fusing agent excludes a colorant other than the metal bis(dithiolene) complex. It may be appropriate to exclude the colorant from the fusing agent when the 3D part to be created is to be the color of the polymeric or polymeric composite build material (e.g., white or off-white) or when a colored ink will be applied to the 3D part.

In some examples, a colored ink can include a colorant, a solvent, a surfactant, and water. In some examples, the fusing agent described herein can further include a colorant.

In some examples, the colored ink(s) can include a pigment, which imparts color to the build material upon application. The pigment may be a self-dispersing pigment or the soft polymer precursor may act as a suitable dispersant for dispersing the pigment throughout the composition. In some examples, the colored ink(s) can include a colorant (e.g., pigment and/or dye) having a color including white or black. Examples of colors include cyan, magenta, yellow, white, black, or mixtures thereof.

The amount of the colorant that may be present in the fusing agent ranges from about 0.1 wt % to about 20 wt % based on the total weight of the fusing agent. In some examples, the amount of the colorant that may be present in the fusing agent ranges from about 1 wt % to about 15 wt % based on the total weight of the fusing agent. In some examples, the amount of the colorant that may be present in the fusing agent ranges from about 1 wt % to about 10 wt % based on the total weight of the fusing agent.

Method(s) of Making Fusing Agent(s)

Also disclosed herein is a method of making the fusing agent.

In some examples, the fusing agent can be made by a method comprising:

exposing a metal bis(dithiolene) complex to a solution comprising at least one electron donor compound, a polar aprotic solvent, and water, and forming a reduced metal bis(dithiolene) complex in the solution, wherein the metal bis(dithiolene) complex has a general formula I:

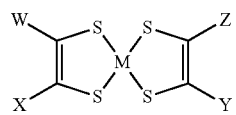

(I)

wherein:

M is a metal selected from the group consisting of nickel, zinc, platinum, palladium, and molybdenum; and each of W, X, Y, and Z is selected from the group consisting of H, Ph, PhR, and SR, wherein Ph is a phenyl group and R is selected from the group consisting of $C_nH_{2n+1}$, $OC_nH_{2n+1}$, and $N(CH_3)_2$, wherein $2 \leq n \leq 12$.

In the method described hereinabove, the at least one electron donor compound can comprise at least one hindered amine light stabilizer compound. In the method described hereinabove, the polar aprotic solvent can be 2-pyrrolidone.

In some examples, the fusing agent may be prepared by exposing the metal bis(dithiolene) complex (I) to a solution including an electron donor compound and a polar aprotic solvent, thereby forming a reduced metal bis(dithiolene) complex and dissolving the reduced metal bis(dithiolene) complex in the solution. In some instances, this solution may also include water. The metal bis(dithiolene) complex (I) may be reduced to its monoanionic form or to its dianionic form by the reducing agent in the solution. The reduced metal bis(dithiolene) complex (I) may then dissolve in the solution.

An example of the method can further include incorporating the solution into a fluid vehicle including a water soluble co-solvent and an additive selected from the group consisting of an emulsifier, a surface tension reduction agent, a wetting agent, a scale inhibitor, an anti-deceleration agent, a chelating agent, an antimicrobial agent, and a combination thereof.

In some examples, the metal bis(dithiolene) complex is exposed to the solution at room temperature (e.g., a temperature ranging from about 18° C. to about 25° C. The metal bis(dithiolene) complex may be reduced and dissolved in the solution within few seconds (e.g., less than 10 seconds).

The adding of the metal bis(dithiolene) complex to a solution including an electron donor compound, a polar aprotic solvent, and water can include mixing, grinding, milling, and combinations thereof to form a substantially homogeneous mixture of the metal bis(dithiolene) complex in the aqueous fusing agent.

Method(s) of Using Fusing Agent(s)

In some examples, a method of using a fusing agent can be described. The method of using the fusing agent can comprise adding the fusing agent described above to a build material deposited on a substrate during 3D printing.

The adding of the fusing agent to the build material can include jetting the fusing agent onto the build material to form a 3D object(s) or part(s).

In some examples, jetting the fusing agent to form 3D object(s) or part(s) can include:

(i) applying a build material;

(ii) pre-heating the build material to a temperature ranging from about 50° C. to about 400° C.;

(iii) selectively applying the fusing agent on at least a portion of the build material;

(iv) exposing the build material and the fusing agent to infrared radiation to form the 3D object(s) or part(s) by fusing the build material and the fusing agent; and (v) repeating (i), (ii), (iii), and/or (iv).

Build Material(s)

The build material can be a powder, a liquid, a paste, or a gel. Examples of build material can include semi-crystalline thermoplastic materials with a wide processing window of greater than 5° C. (e.g., the temperature range between the melting point and the re-crystallization temperature). Some specific examples of the build material can include polyamides (PAs) (e.g., PA 11/nylon 11, PA 12/nylon 12, PA 6/nylon 6, PA 8/nylon 8, PA 9/nylon 9, PA 6,6/nylon 6,6, PA 612/nylon 6,12, PA 8,12/nylon 8,12, PA 9,12/nylon 9,12, or combinations thereof). Other specific examples of the build material can include polyethylene, polyethylene terephthalate (PET), and an amorphous variation of these materials. Still other examples of suitable build materials can include polystyrene, polyacetals, polypropylene, polycarbonate, polyester, thermal polyurethanes, other engineering plastics, and blends of any two or more of the polymers listed herein. Core shell polymer particles of these materials may also be used.

The build material can have a melting point ranging from about 50° C. to about 400° C. As examples, the build material may be a polyamide having a melting point of 180° C., or thermal polyurethanes having a melting point ranging from about 100° C. to about 165° C.

The build material can be made up of similarly sized particles or differently sized particles. In some examples, the build material can include particles of two different sizes. The term "size," as used herein with regard to the build material, refers to the diameter of a spherical particle, or the average diameter of a non-spherical particle (e.g., the average of multiple diameters across the particle).

In an example, the average size of the particles of the build material can ranges from about 0.1 μm to about 100 μm, or from about 1 μm to about 80 μm, or from about 5 μm to about 50 μm.

Build Material Additive(s)

In some examples, the build material can include, in addition to polymer particles, a charging agent, a flow aid, or combinations thereof. Charging agent(s) may be added to suppress tribo-charging. Examples of suitable charging agent(s) include aliphatic amines (which may be ethoxylated), aliphatic amides, quaternary ammonium salts (e.g., behentrimonium chloride or cocamidopropyl betaine), esters of phosphoric acid, polyethylene glycol esters, or polyols. Some suitable commercially available charging agents include HOSTASTAT® FA 38 (natural based ethoxylated alkylamine), HOSTASTAT® FE2 (fatty acid ester), and HOSTASTAT® HS 1 (alkane sulfonate), each of which is available from Clariant Int. Ltd.).

In an example, the charging agent is added in an amount ranging from greater than 0 wt % to less than 5 wt % based upon the total weight of the build material.

Flow aid(s) can be added to improve the coating flowability of the build material. Flow aid(s) may be particularly beneficial when the particles of the build material are less than 25 μm in size. The flow aid can improve the flowability of the build material by reducing the friction, the lateral drag, and the tribocharge buildup (by increasing the particle conductivity). Examples of flow aids can include tricalcium phosphate (E341), powdered cellulose (E460(ii)), magnesium stearate (E470b), sodium bicarbonate (E500), sodium ferrocyanide (E535), potassium ferrocyanide (E536), calcium ferrocyanide (E538), bone phosphate (E542), sodium silicate (E550), silicon dioxide (E551), calcium silicate (E552), magnesium trisilicate (E553a), talcum powder (E553b), sodium aluminosilicate (E554), potassium aluminum silicate (E555), calcium aluminosilicate (E556), bentonite (E558), aluminium silicate (E559), stearic acid (E570), or polydimethylsiloxane (E900).

In an example, the flow aid can be added in an amount ranging from greater than 0 wt % to less than 5 wt % based upon the total weight of the build material.

Jetting Method(s)

In some examples, layer(s) of the build material can be applied in a fabrication bed of a 3D printer. The applied layer(s) can be exposed to heating, which can be performed to pre-heat the build material. Thus, the heating temperature may be below the melting point of the build material. As such, the temperature selected can depend upon the build material that is used. As examples, the heating temperature may be from about 5° C. to about 50° C. below the melting point of the build material. In an example, the heating temperature can range from about 50° C. to about 400° C. In another example, the heating temperature can range from about 150° C. to about 170° C.

Pre-heating the layer(s) of the build material may be accomplished using any suitable heat source that exposes all of the build material to the heat. Examples of the heat source can include a thermal heat source or an electromagnetic radiation source (e.g., infrared (IR), microwave, or combination thereof).

After pre-heating the layer(s) of the build material, the fusing agent herein can be selectively applied on at least a portion of the build material in the layer(s).

The fusing agent described herein can be dispensed from an inkjet printhead, such as a thermal inkjet printhead or a piezoelectric inkjet printhead. The printhead can be a drop-on-demand printhead or a continuous drop printhead.

The printhead may include an array of nozzles through which drops of the fusing agent described herein can be ejected. In some examples, printhead can deliver variable size drops of the fusing agent.

Before or after selectively applying the fusing agent described herein on the portion(s) of the build material, colored ink(s) can be applied to portion(s) of the build material.

After the fusing agent and in some instances the colored ink(s) are selectively applied in the specific portions of the layer(s) of the build material, the entire object(s) or part(s) is exposed to infrared radiation.

The infrared radiation can be emitted from a radiation source, such as an IR (e.g., near-IR) curing lamp, or IR (e.g., near-IR) light emitting diodes (LED), or lasers with specific IR or near-IR wavelengths. Any radiation source may be used that emits a wavelength in the infrared spectrum, for example near-infrared spectrum. The radiation source may be attached, for example, to a carriage that also holds the printhead(s). The carriage may move the radiation source into a position that is adjacent to the fabrication bed containing the 3D printed object(s) or part(s). The radiation source may be programmed to receive commands from a central processing unit and to expose the layer(s) of the build material including the fusing agent to the infrared radiation.

The length of time the radiation is applied for, or energy exposure time, may be dependent, for example, on characteristics of the radiation source, characteristics of the build material, and/or characteristics of the fusing agent(s).

The fusing agent described herein can enhance the absorption of the radiation, convert the absorbed radiation to thermal energy, and promote the transfer of the thermal heat to the build material in contact therewith. In an example, the fusing agent can sufficiently elevate the temperature of the build material above the melting point(s), allowing curing (e.g., sintering, binding, or fusing) of the build material particles to take place.

In some examples, portions of the build material that do not have the fusing agent applied thereto do not absorb enough energy to fuse. However, the generated thermal energy may propagate into the surrounding build material that does not have the fusing agent applied thereto. The propagation of thermal energy may cause at least some of the build material sans fusing agent to partially fuse.

Exposure to radiation can complete the formation of the 3D printed object(s) or part(s).

In some examples, the completed 3D printed object(s) or part(s) may be removed from the fabrication bed and any uncured build material may be removed from the 3D part(s) or object(s).

In some examples, the uncured build material may be washed and then reused.

3D Printing Using Fusing Agent(s)

In some examples, a 3D printing system for forming the 3D object(s) or part(s) can include a supply bed (including a supply of the build material described above), a delivery piston, a roller, a fabrication bed (having a contact surface), and a fabrication piston. Each of these physical elements may be operatively connected to a central processing unit of the 3D printing system. The central processing unit (e.g., running computer readable instructions stored on a non-transitory, tangible computer readable storage medium) can manipulate and transform data represented as physical (electronic) quantities within the printer's registers and memories in order to control the physical elements to create the 3D object(s) or part(s). The data for the selective delivery of the build material described above and the fusing agent described above may be derived from a model of the 3D object(s) or part(s) to be formed.

The delivery piston and the fabrication piston may be the same type of piston, but are programmed to move in opposite directions. In an example, when a first layer of the 3D object(s) or part(s) is to be formed, the delivery piston may be programmed to push a predetermined amount of the build material out of the opening in the supply bed and the fabrication piston may be programmed to move in the opposite direction of the delivery piston in order to increase the depth of the fabrication bed. The delivery piston can advance enough so that when the roller pushes the build material into the fabrication bed and onto the contact surface, the depth of the fabrication bed is sufficient so that a layer of the build material may be formed in the bed. The roller can be capable of spreading the build material into the fabrication bed to form the layer, which is relatively uniform in thickness. In an example, the thickness of the layer can range from about 1 µm to about 1000 µm, although thinner or thicker layers may also be used.

In some examples, the roller can be replaced by other tools, such as a blade that may be used for spreading different types of powders, or a combination of a roller and a blade.

After the layer of the build material is deposited in the fabrication bed, the layer can be exposed to heating. Heating can be performed to pre-heat the build material, and thus a heating temperature below the melting point of the build material can be useful. As such, the temperature selected can depend upon the build material that is used. As examples, the heating temperature may be from about 5° C. to about 50° C. below the melting point of the build material. In an example, the heating temperature can range from about 50° C. to about 400° C. In another example, the heating temperature can range from about 150° C. to about 170° C.

Pre-heating the layer of the build material may be accomplished using any suitable heat source that exposes all of the build material in the fabrication bed to the heat. Examples of the heat source include a thermal heat source or an electromagnetic radiation source (e.g., infrared (IR), microwave, or combinations thereof).

After pre-heating the layer, the fusing agent can be selectively applied on a portion of the build material in the layer. The fusing agent may be dispensed from an inkjet printhead. One or multiple printheads may be used that span the width of the fabrication bed. The printhead may be attached to a moving XY stage or a translational carriage that moves the printhead adjacent to the fabrication bed in order to deposit the fusing agent in targeted area(s).

The printhead may be programmed to receive commands from the central processing unit and to deposit the fusing agent according to a pattern of a cross-section for the layer of the 3D object(s) or part(s) that is to be formed. As used herein, the cross-section of the layer of the object(s) or part(s) to be formed refers to the cross-section that is parallel to the contact surface.

In an example, the printhead can selectively apply the fusing agent on those portion(s) of the layer that are to be fused to become the first layer of the 3D object(s) or part(s). As an example, if the first layer is to be shaped like a cube or cylinder, the fusing agent can be deposited in a square pattern or a circular pattern, respectively, on at least a portion of the layer of the build material.

Examples of fusing agents include water-based dispersions having a radiation absorbing binding agent (e.g., an active material). The active material may be a near infrared light absorber.

In the examples described herein, the active material is the metal bis(dithiolene) complex described hereinabove. In some examples, the dye or pigment in the fusing agent can include any color in addition to the metal bis(dithiolene) complex described hereinabove.

The aqueous nature of the fusing agent can allow the fusing agent to penetrate, at least partially, into the layer of the build material. The build material may be hydrophobic, and the presence of a co-solvent and/or a surfactant in the fusing agent may assist in obtaining wetting behavior.

It is to be understood that a single fusing agent may be selectively applied to form the layer of the 3D object(s) or part(s), or multiple fusing agents may be selectively applied to form the layer of the 3D object(s) or part(s).

After the fusing agent is/are selectively applied on the targeted portion(s), a detailing agent may be selectively applied on the same and/or on different portion(s) of the build material. The detailing agent can include a colorant, a surfactant, a co-solvent, and a balance of water. In some examples, the detailing agent can include these components, and no other components. In some instances, the detailing agent can exclude specific components, such as additional colorants (e.g., pigment(s)). In some other examples, the detailing agent can further include an anti-kogation agent, a biocide, or combinations thereof. The detailing agent can prevent or reduce cosmetic defects (e.g., color and white patterns) by adding the colorant, which diffuses into and dyes the build material particles at least at the edge boundary.

The colorant in the detailing agent may be a dye of any color having substantially no absorbance in a range of 650 nm to 2500 nm. By "substantially no absorbance" it is meant that the dye absorbs no radiation having wavelengths in a range of 650 nm to 2500 nm, or that the dye absorbs less than 10% of radiation having wavelengths in a range of 650 nm to 2500 nm. The dye can also be capable of absorbing radiation with wavelengths of 650 nm or less. As such, the dye in the detailing agent can absorb at least some wavelengths within the visible spectrum, but absorb little or no wavelengths within the near-infrared spectra. This is in contrast to the active material in the fusing agent, which can absorbs wavelengths within the near-infrared spectra. As such, the colorant in the detailing agent may not substantially absorb the fusing radiation, and thus may not initiate melting and fusing of the build material in contact therewith when the layer is exposed to the fusing radiation.

The dye selected as the colorant in the detailing agent can also have a high diffusivity (e.g., penetrates into greater than 10 µm and up to 100 µm of the build material particle). The high diffusivity can allow the dye to penetrate into the build material particles upon which the detailing agent can be applied, and also enable the dye to spread into portions/areas of the build material that are adjacent to the portions/areas of the build material upon which the detailing agent is applied. The dye can penetrates into the build material particles to dye/color the particles. When the detailing agent is applied at or just outside the edge boundary, the build material particles at the edge boundary may be colored. At least some of these dyed build material particles can be present at the edge(s) or surface(s) of the formed 3D layer or object(s)/part(s), which can prevent or reduce any patterns from forming at the edge(s) or surface(s).

The above 3D printing stages can be repeated in different orders to obtain the 3D printed object(s) or part(s).

In some examples, the detailing agent described above can be the same as the colored ink(s) described above.

Unless otherwise stated, any feature described hereinabove can be combined with any example or any other feature described herein.

In describing and claiming the examples disclosed herein, the singular forms "a," "an," and "the" include plural referents unless the context clearly dictates otherwise.

It is to be understood that concentrations, amounts, and other numerical data may be expressed or presented herein in range formats. It is to be understood that such range formats are used merely for convenience and brevity and thus should be interpreted flexibly to include not just the numerical values explicitly recited as the end points of the range, but also to include all the individual numerical values or sub-ranges encompassed within that range as if each numerical value and sub-range is explicitly recited. As an illustration, a numerical range of "about 1 wt % to about 5 wt %" should be interpreted to include not just the explicitly recited values of about 1 wt % to about 5 wt %, but also include individual values and subranges within the indicated range. Thus, included in this numerical range are individual values such as 2, 3.5, and 4 and sub-ranges such as from 1-3, from 2-4, and from 3-5, etc. This same applies to ranges reciting a single numerical value.

Reference throughout the specification to "one example," "some examples," "another example," "an example," and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

Unless otherwise stated, references herein to "wt %" of a component are to the weight of that component as a percentage of the whole composition comprising that component. For example, references herein to "wt %" of, for example, a solid material such as polyurethane(s) or colorant(s) dispersed in a liquid composition are to the weight percentage of those solids in the composition, and not to the amount of that solid as a percentage of the total non-volatile solids of the composition.

If a standard test is mentioned herein, unless otherwise stated, the version of the test to be referred to is the most recent at the time of filing this patent application.

All amounts disclosed herein and in the examples below are in wt % unless indicated otherwise.

To further illustrate the present disclosure, examples are given herein. It is to be understood that these examples are presented for illustrative reasons and are not to be construed as limiting the scope of the present disclosure.

EXAMPLES

Example 1

An example of the metal bis(dithiolene) complex was prepared in an example of the polar aprotic solvent and an example of the electron donor compound(s) (referred to as "Composition 1"). The metal bis(dithiolene) complex used was nickel dithiolene. The polar aprotic solvent used was 2-pyrrolidone, and the electron donor compound(s) used was TINUVIN® 770 (i.e., bis(2,2,6,6,-tetramethyl-4-piperidyl)sebacate). The general formulation of the composition is shown in Table 1, with the wt % of each component that was used.

TABLE 1

| Ingredient | Specific component | Composition 1 (wt %) |
|---|---|---|
| Polar aprotic solvent | 2-pyrrolidone | 80 |
| Electron donor compound(s) | TINUVIN ® 770 | 7 |
| Metal bis(dithiolene) complex | Nickel dithiolene | 3 |
| Solvent | Butanol | 10 |

The nickel dithiolene, in the presence of TINUVIN® 770, was readily reduced and dissolved in the 2-pyrrolidone within about 20 seconds at room temperature. The nickel dithiolene changed colors from green (before reduction) to reddish brown after reduction to its monoanionic form and then to colorless after reduction to its dianionic form.

Example 2

Composition 1 summarized in Table 1 above was incorporated into a fluid vehicle to form a fusing agent. The general formulation of the vehicle is shown in Table 2, with the wt % of each component that was used.

TABLE 2

| Ingredient | Specific component | Vehicle (wt %) |
|---|---|---|
| Co-solvent | 2-pyrrolidone | 40 |
| Emulsifier | CRODAFOS ® O3A | 1 |
| Surface tension reduction agent | SURFYNOL ® SEF | 1.5 |
| Wetting agent | CAPSTONE ® FS-35 | 0.10 |
| Scale inhibitor/ Anti-deceleration agent | DOWFAX ™ 2A1 | 0.20 |
| Chelating agent | TRILON ® M | 0.08 |
| Biocide | PROXEL ® GXL | 0.36 |
| Water | DI (deionized) Water | Balance |

The fusing agent included about 50% of Composition 1, about 40% of the vehicle, and about 10% of additional deionized water (in addition to the water already present in the vehicle).

The measured viscosity of the fusing agent in this Example 2 was 0.9 g/cm$^3$.

The fusing agent composition emanated no rotten egg smell.

This fusing agent also showed no phase separation (see FIG. 1A).

Comparative Example 1

An example of the metal bis(dithiolene) complex was prepared in an example of the polar aprotic solvent and an example of the electron donor compound(s) (referred to as "Comparative Composition 1"). The metal bis(dithiolene) complex used was nickel dithiolene. The polar aprotic solvent used was hydroxyethyl-2-pyrrolidone, and the electron donor compound(s) used was TINUVIN® 770 (i.e., bis(2,2,6,6,-tetramethyl-4-piperidyl)sebacate). The general formulation of the composition is shown in Table 3, with the wt % of each component that was used.

TABLE 3

| Ingredient | Specific component | Comparative Composition 1 (wt %) |
|---|---|---|
| Polar aprotic solvent | hydroxyethyl-2-pyrrolidone | 80 |
| Electron donor compound(s) | TINUVIN ® 770 | 7 |
| Metal bis(dithiolene) complex | Nickel dithiolene | 3 |
| Solvent | Butanol | 10 |

Comparative Composition 1 summarized in Table 3 above was incorporated into a fluid vehicle to form a fusing agent. The general formulation of the vehicle is shown in Table 4, with the wt % of each component that was used.

TABLE 4

| Ingredient | Specific component | Vehicle (wt %) |
|---|---|---|
| Co-solvent | Hydroxythyl-2-Pyrrolidone | 40 |
| Emulsifier | CRODAFOS ® O3A | 1 |
| Surface tension reduction agent | SURFYNOL ® SEF | 1.5 |
| Wetting agent | CAPSTONE ® FS-35 | 0.10 |
| Scale inhibitor/Anti-deceleration agent | DOWFAX ™ 2A1 | 0.20 |
| Chelating agent | TRILON ® M | 0.08 |
| Biocide | PROXEL ® GXL | 0.36 |
| Water | DI (deionized) Water | Balance |

The fusing agent included about 50% of Comparative Composition 1, about 40% of the vehicle, and about 10% of additional deionized water (in addition to the water already present in the vehicle).

The measured viscosity of the fusing agent in this Comparative Example 1 was 1.2 g/cm$^3$.

Comparative Example 2

An example of the metal bis(dithiolene) complex was prepared in an example of the polar aprotic solvent and an example of a reducing compound (referred to as "Comparative Composition 2"). The metal bis(dithiolene) complex used was nickel dithiolene. The polar aprotic solvent used was 2-pyrrolidone and the reducing compound was dodecanethiol. The general formulation of the composition is shown in Table 5, with the wt % of each component that was used.

TABLE 5

| Ingredient | Specific component | Comparative Composition 2 (wt %) |
|---|---|---|
| Polar aprotic solvent | 2-pyrrolidone | 80 |
| Reducing Compound | Dodecanethiol | 7 |
| Metal bis(dithiolene) complex | Nickel dithiolene | 3 |
| Solvent | Butanol | 10 |

Comparative Composition 2 summarized in Table 5 above was incorporated into a fluid vehicle to form a fusing agent. The general formulation of the vehicle is shown in Table 6, with the wt % of each component that was used.

TABLE 6

| Ingredient | Specific component | Vehicle (wt %) |
|---|---|---|
| Co-solvent | Hydroxythyl-2-Pyrrolidone | 40 |
| Emulsifier | CRODAFOS ® O3A | 1 |
| Surface tension reduction agent | SURFYNOL ® SEF | 1.5 |
| Wetting agent | CAPSTONE ® FS-35 | 0.10 |
| Scale inhibitor/Anti-deceleration agent | DOWFAX ™ 2A1 | 0.20 |
| Chelating agent | TRILON ® M | 0.08 |
| Biocide | PROXEL ® GXL | 0.36 |
| Water | DI (deionized) Water | Balance |

The fusing agent included about 50% of Comparative Composition 2, about 40% of the vehicle, and about 10% of additional deionized water (in addition to the water already present in the vehicle).

The obtained fusing agent emanated a rotten egg smell. It is believed that this composition emanated a rotten egg smell because of the presence of the dodecanethiol to reduce the metal bis(dithiolene) complex.

Figure 1B:

This fusing agent also showed phase separation due to the presence of dodecanethiol (see FIG. 1B).

The above examples show that when the fusing agent replaces hydroxyethyl-2-pyrrolidone with 2-pyrrolidone, the composition is less viscous and can therefore generate better thermal inkjet performance.

The above examples further show that when dodecanethiol is replaced with an electron donor compound (e.g., hindered amine light stabilizers such as TINUVIN family of compounds—TINUVIN® 770), phase separation is reduced and issues with rotten egg smell emanation are eliminated.

The electron donor compounds described herein (e.g., hindered amine light stabilizers) can also stabilize the build material against degradation by photo-oxidation after a 3D printed part or object is obtained.

While several examples have been described in detail, it is to be understood that the disclosed examples may be modified. Therefore, the foregoing description is to be considered non-limiting.

What is claimed is:
1. A fusing agent comprising:
   a reduced form of metal bis(dithiolene) complex, wherein the reduced form of the metal bis(dithiolene) complex is formed from a metal bis(dithiolene) complex that has a general formula I

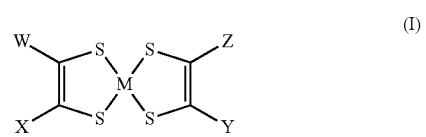

(I)

wherein M is a metal selected from a group consisting of nickel, zinc, platinum, palladium, and molybdenum and each of W, X, Y, and Z is selected from a group consisting of H, Ph, PhR, and SR, wherein Ph is a phenyl group and R is selected from a group consisting of $C_nH_{2n+1}$, $OC_nH_{2n+1}$, and $N(CH_3)_2$, wherein $2 \leq n \leq 12$;

at least one electron donor compound, wherein the at least one electron donor compound comprises at least one hindered amine light stabilizer compound;
a thiol surfactant;
a polar aprotic solvent present in an amount sufficient to reduce the metal bis(dithiolene) complex to the reduced form in a monoanionic form or in a dianionic form; and
water, wherein the metal bis(dithiolene) complex is present in an amount about 1 wt % to about 10 wt %, the at least one electron donor compound is present in an amount about 1 wt % to about 10 wt %, the thiol surfactant is present in an amount about 3 wt % to 5 wt %, and the polar aprotic solvent is present in an amount about 5 wt % to about 50 wt %, wherein the amounts are based on a total weight of the fusing agent.

2. The fusing agent according to claim 1, wherein the at least one hindered amine light stabilizer compound comprises bis(2,2,6,6,-tetramethyl-4-piperidyl)sebacate.

3. The fusing agent according to claim 1, wherein the polar aprotic solvent is selected from the group consisting of 1-methyl-2-pyrrolidone, 2-pyrrolidone, 1-(2-hydroxyethyl)-2-pyrrolidone, dimethylformamide (DMF), dimethyl sulfoxide (DMSO), and a combination thereof.

4. The fusing agent according to claim 1, further comprising a colorant.

5. The fusing agent according to claim 1, wherein the fusing agent is added to a build material deposited on a substrate during three-dimensional printing.

6. A method for making a fusing agent, comprising:
exposing a metal bis(dithiolene) complex to a solution comprising at least one electron donor compound, a polar aprotic solvent present in an amount sufficient to reduce the metal bis(dithiolene) complex to a reduced form in a monoanionic form or in a dianionic form, a thiol surfactant, and water, wherein the at least one electron donor compound comprises at least one hindered amine light stabilizer compound, wherein the metal bis(dithiolene) complex is present in an amount about 1 wt % to about 10 wt %, the at least one electron donor compound is present in an amount about 1 wt % to about 10 wt %, the thiol surfactant is present in an amount about 3 wt % to 5 wt %, and the polar aprotic solvent is present in an amount about 5 wt % to about 50 wt %, wherein the amounts are based on a total weight of the fusing agent; and
forming the reduced form of the metal bis(dithiolene) complex in the solution,
wherein the metal bis(dithiolene) complex has a general formula I:

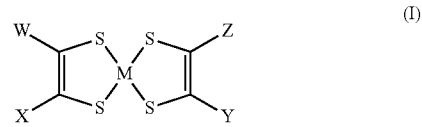

wherein:
M is a metal selected from the group consisting of nickel, zinc, platinum, palladium, and molybdenum; and
each of W, X, Y, and Z is selected from the group consisting of H, Ph, PhR, and SR, wherein Ph is a phenyl group and R is selected from the group consisting of $C_nH_{2n+1}$, $OC_nH_{2n+1}$, and $N(CH_3)_2$, wherein $2 \leq n \leq 12$.

7. The method according to claim 6, wherein the polar aprotic solvent is selected from the group consisting of 1-methyl-2-pyrrolidone, 2-pyrrolidone, 1-(2-hydroxyethyl)-2-pyrrolidone, dimethylformamide (DMF), dimethyl sulfoxide (DMSO), and a combination thereof.

8. The method according to claim 7, wherein the polar aprotic solvent is 2-pyrrolidone.

9. The method according to claim 6, wherein the at least one hindered amine light stabilizer compound comprises bis(2,2,6,6,-tetramethyl-4-piperidyl)sebacate.

10. The method according to claim 6,
wherein the at least one electron donor compound comprises at least one hindered amine light stabilizer compound, and
wherein the polar aprotic solvent is 2-pyrrolidone.

* * * * *